United States Patent
Hector et al.

(10) Patent No.: US 9,636,448 B2
(45) Date of Patent: *May 2, 2017

(54) RECIRCULATION DEVICE OF AN EXTRACORPOREAL BLOOD TREATMENT APPARATUS

(71) Applicant: B. BRAUN AVITUM AG, Melsungen (DE)

(72) Inventors: Rainer Hector, Osnabrueck (DE); Charleen Hundertmark, Kassel (DE); Judith Hieronymi, Gudensberg (DE); Michele Susca, Dossenheim (DE); Anne-Marie Mihailescu, Melsungen (DE); Claudia Freitag, Gudensberg (DE)

(73) Assignee: B. BRAUN AVITUM AG, Melsungen (DE)

( * ) Notice: Subject to any disclaimer, the term of this patent is extended or adjusted under 35 U.S.C. 154(b) by 10 days.

This patent is subject to a terminal disclaimer.

(21) Appl. No.: 14/784,822

(22) PCT Filed: Apr. 16, 2014

(86) PCT No.: PCT/EP2014/057749
§ 371 (c)(1),
(2) Date: Oct. 15, 2015

(87) PCT Pub. No.: WO2014/170382
PCT Pub. Date: Oct. 23, 2014

(65) Prior Publication Data
US 2016/0058936 A1    Mar. 3, 2016

(30) Foreign Application Priority Data
Apr. 19, 2013 (DE) .................. 10 2013 103 986

(51) Int. Cl.
*A61M 37/00* (2006.01)
*A61M 1/36* (2006.01)
(Continued)

(52) U.S. Cl.
CPC .......... *A61M 1/3647* (2014.02); *A61M 1/367* (2013.01); *A61M 1/3643* (2013.01);
(Continued)

(58) Field of Classification Search
CPC .. A61M 1/3647; A61M 1/3643; A61M 1/367; A61M 39/223; F16K 11/02; F16K 11/072; F16K 15/18; F16K 31/60
(Continued)

(56) References Cited

U.S. PATENT DOCUMENTS

| | | | |
|---|---|---|---|
| 3,827,601 A | 8/1974 | Magrath | |
| 4,397,335 A | 8/1983 | Doblar | |

(Continued)

FOREIGN PATENT DOCUMENTS

| | | |
|---|---|---|
| CA | 2807013 | 2/2012 |
| CN | 1809393 | 7/2006 |

(Continued)

OTHER PUBLICATIONS

German Search Report for German Application No. 10 2013 103 986.3 mailed Oct. 16, 2013, including partial translation.
(Continued)

*Primary Examiner* — Philip R Wiest
(74) *Attorney, Agent, or Firm* — RatnerPrestia

(57) ABSTRACT

A recirculation device of an extracorporeal blood treatment device is disclosed with a preferably universal medical fluid container to which an arterial line section of a fluid conducting system of the extracorporeal blood treatment device can be connected as an option. Furthermore, the recirculation device has a 3-way switch, preferably a 3-way valve, (Continued)

which is arranged directly downstream of the universal medical fluid container. A conduit of the 3-way switch is preferably coupled with a spike or a similar connecting device or is formed in one piece together with it.

10 Claims, 2 Drawing Sheets

(51) Int. Cl.
  *A61M 39/22* (2006.01)
  *F16K 11/02* (2006.01)
  *F16K 15/18* (2006.01)
  *F16K 31/60* (2006.01)
  *F16K 11/072* (2006.01)

(52) U.S. Cl.
  CPC ........... *A61M 39/223* (2013.01); *F16K 11/02* (2013.01); *F16K 11/072* (2013.01); *F16K 15/18* (2013.01); *F16K 31/60* (2013.01)

(58) Field of Classification Search
  USPC .............................................. 604/4.01–6.11
  See application file for complete search history.

(56) References Cited

U.S. PATENT DOCUMENTS

| | | | |
|---|---|---|---|
| 4,819,653 A | 4/1989 | Marks | |
| 4,844,810 A | 7/1989 | Richalley | |
| 5,259,961 A | 11/1993 | Eigendorf | |
| 5,334,315 A | 8/1994 | Matkovich | |
| 5,540,653 A | 7/1996 | Schock | |
| 5,669,879 A | 9/1997 | Duer | |
| 8,343,098 B2 | 1/2013 | Nystrom et al. | |
| 8,617,093 B2 | 12/2013 | Kopperschmidt et al. | |
| 9,486,569 B2* | 11/2016 | Eikelmann | A61M 1/3647 |
| 2003/0125673 A1* | 7/2003 | Houde | F16K 11/0856 604/246 |
| 2010/0191106 A1 | 7/2010 | Koyama | |
| 2011/0137224 A1 | 6/2011 | Ibragimov | |
| 2011/0208128 A1 | 8/2011 | Wu | |
| 2013/0131609 A1 | 5/2013 | Kawashima | |
| 2013/0139901 A1 | 6/2013 | Haecker et al. | |

FOREIGN PATENT DOCUMENTS

| | | |
|---|---|---|
| CN | 102458503 | 5/2012 |
| CN | 202655890 | 9/2012 |
| CN | 103002933 | 3/2013 |
| CN | 103052416 | 4/2013 |
| DE | 4208274 | 10/1993 |
| EP | 2158934 | 3/2010 |
| WO | 8806895 | 9/1988 |

OTHER PUBLICATIONS

International Search Report for International Application No. PCT/EP2014/057744 mailed Aug. 8, 2014.
International Search Report for International Application No. PCT/EP2014/057745 mailed Aug. 7, 2014.
International Search Report for International Application No. PCT/EP2014/057749 mailed Jul. 31, 2014.
Chinese Office Action and Search Report for CN 201480022287.6, with translation, dated May 25, 2016.
Chinese Office Action and Search Report for CN 201480022273.4, with translation, dated Jun. 15, 2016.
Notice of Allowance for U.S. Appl. No. 14/783,266 dated Aug. 26, 2016.

* cited by examiner

RECIRCULATION DEVICE OF AN EXTRACORPOREAL BLOOD TREATMENT APPARATUS

CROSS REFERENCE TO RELATED APPLICATIONS

This application is the U.S. national phase application of PCT International Application No. PCT/EP2014/057749 filed Apr. 16, 2014, which claims priority to German Patent Application No. DE 10 2013 103 986.3 filed Apr. 19, 2013, the contents of each application being incorporated by reference herein.

FIELD OF THE INVENTION

The invention in hand concerns the recirculation device of an extracorporeal blood treatment device, in particular a dialysis machine, according to the independent claim.

BACKGROUND OF THE INVENTION

The hydraulic system of a blood treatment device, for example a dialysis machine, has to be filled with fluid, for example an NaCl solution, before being connected up to a patient, in such a way that air pockets in the system that would be dangerous for a patient connected up to the fluids of the system are eliminated. Furthermore, the hydraulic system can be flushed with the filled-in fluid for a certain period of time in order to filter/wash out any contaminants, dirt particles, etc. that may have deposited in the system before the system is connected up to the patient. On an extracorporeal blood treatment device, these two procedures are performed in the scope of a filling-recirculation cycle.

In the state of the art, there are fluid containers, preferably in the shape of plastic bags, that are specially designed for extracorporeal blood treatment devices of this relevant type in order to enable, among others, the device functions as defined above. This kind of fluid containers is also manufactured and sold by the applicant filing the application in hand.

As a rule, such a fluid container has a fluid intake chamber and two preferably closable fluid connectors. On a first of the two connectors, an arterial line section, and on the second connector, a venous line section of the hydraulic system (fluid system) of the extracorporeal blood treatment device can be connected. The fluid bag as well as the two line sections together constitute a recirculation device of the extracorporeal blood treatment device.

For the fluid system filling process, first the arterial line section is connected to the first fluid connector of the bag, and after opening of the first fluid connector, the hydraulic system is filled. The venous line section of the system first remains open to the atmosphere (or is connected to a drain) so that air inside the system can escape/be vented in the atmosphere. As soon as the filling process is completed, the venous line section is connected to the second fluid connector of the bag in order to recirculate the fluid inside the hydraulic system of the extracorporeal blood treatment device for a certain period of time or a certain volume of flow through the bag chamber then.

During this recirculation process, the fluid flows through internal system filter devices in which possibly present contaminations and/or remaining air pockets are removed/filtered out with the fluid, which arise, for example, during the manufacturing of the system components such as hoses, valves, etc., and can get deposited in the system. Finally the venous line section of the hydraulic system is again disconnected from the second fluid connector of the fluid bag and the fluid contained in the hydraulic system is once again flushed out under constant supply of fluid from the container.

Upon termination of the recirculation process, the filling/recirculation cycle preparing for patient treatment is completed so that the two line sections (venous and arterial) can be disconnected from the fluid bag and connected up to the patient for treatment.

The description above of the filling/recirculation cycle of a hydraulic system/fluid conducting system of an extracorporeal blood treatment device (dialysis machine) known from the state of the art indicates that the fluid bag remains in the system circuit for the filling and recirculation processes, i.e. that the fluid inside the system is circulated through the fluid bag and/or its fluid chamber and consequently contaminates the fluid inside the fluid bag on a regular basis. The consequence of this is that with each new treatment preparation of the extracorporeal blood treatment device, a new fluid bag with fresh, uncontaminated fluid has to be used for the following filling/recirculation cycle, whereas the fluid bag for the filling/recirculation cycle performed before is disposed of independently of its residual content. It is obvious that this procedure results in the wasting of a large quantity of fluid in case of a high patient treatment number because the fluid content of a fluid bag can only be used (incompletely) for one filling/recirculation cycle.

SUMMARY OF THE INVENTION

In view of these problems, an object of the invention in hand is to provide a recirculation device of an extracorporeal blood treatment device that can be operated more efficiently and thus more cost-efficiently as compared to the state of the art.

This object is solved by a recirculation device of an extracorporeal blood treatment device with the characteristics of the independent claim. Advantageous embodiments of the invention are the subject matter of sub-claims.

The core of the invention in hand is the equipment of the class-specific recirculation device (means for recirculating fluid) of an extracorporeal blood treatment device with a 3-way switch (means), for example a Y or T piece or a 3-way valve, whereby the conduits can optionally be shut off (for example with hose clamps (hose clamping means) on the conduits or with the valve) in order to close off the switch completely and/or to fluidically connect the conduits optionally and/or to allow a fluid flow at least between two selected conduits. According to aspects of the invention, the 3-way switch, preferably the 3-way valve, is arranged directly downstream of this one, preferably universal medical fluid container (means for storing medical fluid). In the specific case, a first connector of the 3-way switch (of the 3-way valve) is preferably coupled with a so-called spike or a different connecting device/means or is designed as such, with which a fluid chamber of the fluid container can be tapped. To a second connector of the 3-way switch (of the 3-way valve), an arterial line section, and to a third connector of the 3-way switch (of the 3-way valve), a venous line section can be connected. The 3-way switch (preferably the 3-way valve) can preferably be put and/or switched manually in at least three positions, of which in a first switch position, the first connector is exclusively fluidically connected with the second connector and/or a fluid flow between these two connectors is possible and the third connector is closed (single-pass switch position), in a second switch position, the second connector is fluidically connected with the third connector and/or a fluid flow between these two connectors is possible and the first connector is closed (recirculation switch position), and in a third switch position, all three connectors are disconnected from each other and/or closed.

A recirculation device/means equipped in such a way enables the coupling of the fluid container with the arterial line section for the filling process by putting the 3-way switch, preferably the 3-way valve, in the first switch position, and connecting the arterial line section with the venous line section for the recirculation process by putting the 3-way switch, preferably the 3-way valve, in the second switch position. As the first connector of the 3-way switch, preferably the 3-way valve, is closed in this second switch position, the fluid bag is disconnected from the hydraulic system/circuit of the extracorporeal blood treatment device so the remaining fluid in it is not contaminated by the fluid recirculating in the hydraulic system. As in the third switch position of the 3-way switch, preferably the 3-way valve, all of its connectors are closed, the two line sections of the hydraulic system can be disconnected in this switch position and connected to the patient for treatment.

As a result, the fluid container can be used for several subsequent treatments depending on the fill volume so that no fluid is lost any more. Furthermore, the recirculation device can be equipped with a conventional/universal medical fluid container, which is more cost-efficient in comparison with the specially designed containers with two connectors for extracorporeal blood treatment devices. Finally, the fluid container used does not require any connector, in particular for the case that a so-called spike is connected to the 3-way switch, preferably the 3-way valve, or is combined with it into an integral modular unit. In the latter case, the spike can be connected effectively transition-free, i.e. without interposition of a (bridging) line section, directly with the first connector, preferably in one piece.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

According to FIG. 1, an extracorporeal blood treatment device 1, for example a dialysis machine, has an internal hydraulic conducting system (hereinafter referred to as fluid conducting system) through which during a treatment phase on the machine side, for example, a blood purification fluid (dialysis fluid) is passed, and on the patient side, blood flows through it extracorporeally, whereby the machine-side and the patient-side fluid conducting systems are fluidically separated in case of a dialysis machine by a dialyser (filter) that is not shown in more detail.

For this purpose, the fluid conducting system has a venous line section and an arterial line section 2, 4 on the patient side, preferably with connectors 6, 8 on each hose section arranged/formed on the ends in each case to which, for example, injection needles or cannulas (not depicted) can be connected as patient access, which can be introduced in a patient's body.

In order to avoid a washing out of any contamination due to manufacturing, in particular in the patient-side fluid conducting system, the extracorporeal blood treatment device 1 has a recirculation device with which the fluid conducting system is cleaned before every patient treatment as a rule.

Figure 1:
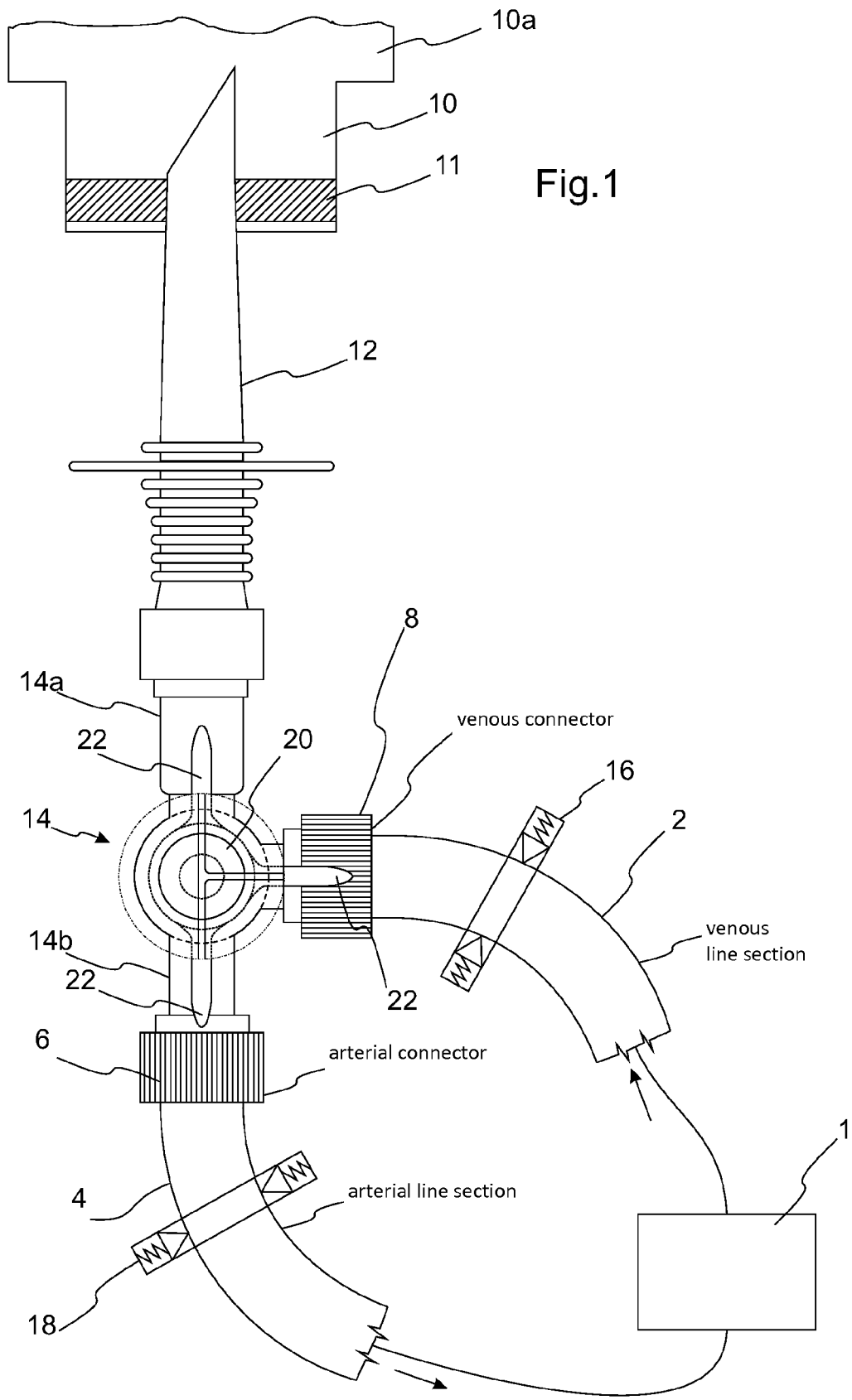
FIG. 1 shows a recirculation device of an extracorporeal blood treatment device according to a preferred exemplary embodiment of the invention.

According to FIG. 1, the recirculation device according to aspects of the invention in hand has a fluid source, preferably in the form of a universal fluid container 10, with a single outlet 11, which is punctured in the exemplary embodiment in hand with a spike 12 in order to tap fluid from the fluid container 10. The design of spike 12 matches the one of known spike structures so that its design does not have to be explained in more detail here. Furthermore, it is to be pointed out that, for example, in case of a Luer-Lock or another fitting on the container side, the spike may be replaced by a suitable connecting piece on the side of the recirculation device.

Furthermore the recirculation device according to aspects of the invention has a 3-way switch, preferably a 3-way valve 14, which is arranged directly downstream of the spike 12 (connecting piece) in the direction of flow away from the fluid container 10. In the case in hand, the spike 12 is directly (without interposition of an additional line section) connected to the 3-way valve 14. As an alternative, the spike 12 can also be realised in one piece or as a modular unit with the 3-way valve.

For that purpose, the 3-way valve 14 has a first connector or fluid inlet 14a that is fluidically connected with the spike 12 and/or to which the fluid source 10 can be connected/is connected. Furthermore, the 3-way valve 14 has a second connector 14b, to which the arterial line section 4 of the patient-side fluid conducting system of the extracorporeal blood treatment device 1 can be connected. Finally, the 3-way valve 14 has a third connector 14c, to which the venous line section 2 of the patient-side fluid conducting system of the extracorporeal blood treatment device 1 can be connected. The venous line section as well as the arterial line section 2, 4 are each equipped with a hose clamp 16, 18 or a similar blocking mechanism in order to close the respective hose section temporarily as an option.

The 3-way valve 14 in hand has a manually operable rotary lock consisting of a rotating cylindrical valve piston 20 that is equipped/designed on the front side with a handle, preferably in the shape of (three) intervention vanes 22. The valve piston has a central longitudinal bore, of which three radial bores branch off at equal distances in circumferential direction. The intervention vanes 22 are arranged in such a way that they are aligned along the radial bores and so indicate the flow direction of the radial bores. Such a 3-way valve is sufficiently known from the state of the art so that a further description, in particular of its function, can be dispensed with here.

FIGS. 2 to 5 show the switch positions intended according to aspects of the invention of the 3-way valve 14 in dependence on the current operating phases of the extracorporeal blood treatment device 1, which are described below in connection with the functions intended to be performed with it.

Figure 2:
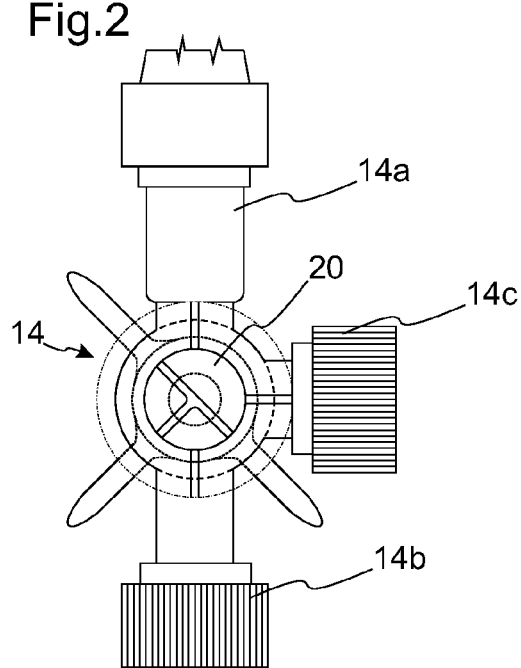
FIG. 2 shows a closed switch position of a 3-way valve of the recirculation device according to FIG. 1 as a possible variant of the 3-way switch according to aspects of the invention, whereby it is already pointed out here that, for example, a Y- or T-piece with hose blocking mechanism (hose clamps) can be provided on each branch conduit.

According to FIG. 2, the 3-way valve 14 is shown in a shut-off position in which all three connectors 14a-14c are closed. In this switch position, the spike 12 can puncture the outlet 12 of the universal fluid container 10 and so tap the fluid stored in there (in the chamber 10a formed by the container) without losing fluid into the atmosphere.

Figure 3:
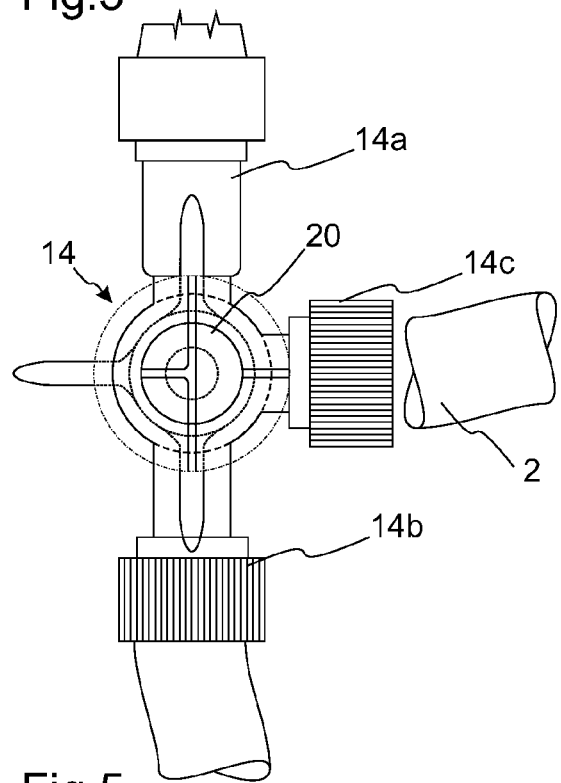
FIG. 3 shows a "single-pass" switch position of the 3-way valve of the recirculation device according to FIG. 1, in which a fluid source (fluid container) is exclusively fluidically connected with an arterial line section of the extracorporeal blood treatment device.

FIG. 3 shows the so-called "single-pass" switch position in which the first connector 14a is fluidically connected with the second connector 14b, while the third connector 14c is closed. In this switch position, the arterial line section 4 is already connected to the second connector 14b, but the venous line section 2 is open to the atmosphere or connected to a drain/receiver tank.

In this switch position, fluid (NaCl solution) is passed through the 3-way valve 14 in the arterial line section 4 and so the patient-side fluid conducting system is flooded constantly until the fluid runs out of the venous line section 2. This means that the venous line section 2 serves as air vent during this system filling process. It has to be pointed out that the hose clamps 16, 18 are naturally open during this process.

Figure 4:
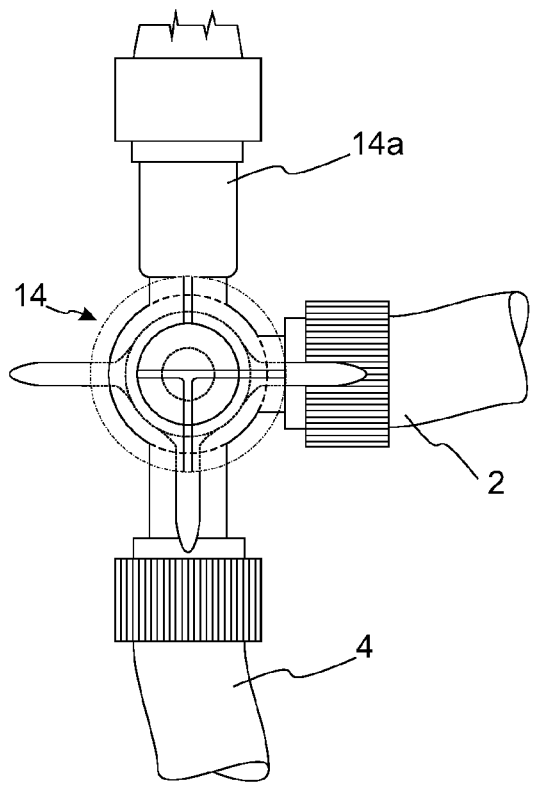
FIG. 4 shows a "recirculation" switch position of the 3-way valve of the recirculation device according to FIG. 1, in which the arterial line section is exclusively fluidically connected (short-circuited) with a venous line section of the extracorporeal blood treatment device and the fluid source is fluidically separated from the extracorporeal blood treatment device.
Figure 5:
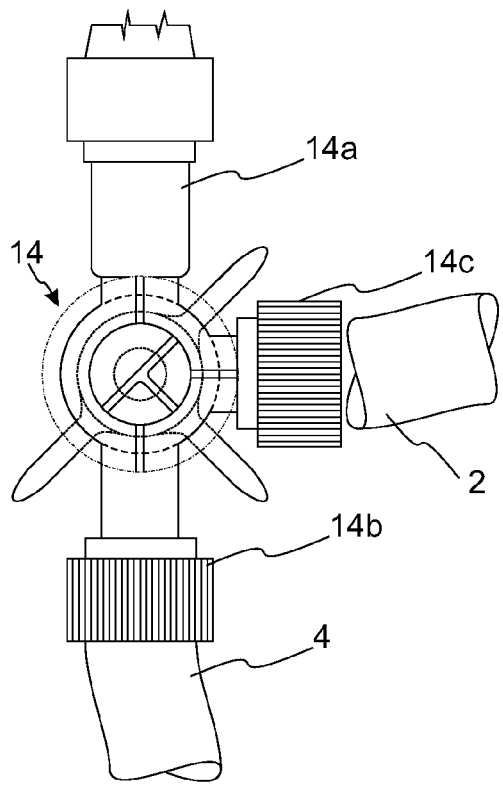
FIG. 5 shows another closed switch position of a 3-way valve of the recirculation device according to FIG. 1.

As soon as the system has been filled with fluid from the fluid container 10, the venous line section is connected to the third connector 14c of the 3-way valve 14, and the 3-way valve 14 is put in the switch position according to FIG. 4, which can be referred to as "recirculation" switch position. In this switch position, the second and third connectors 14b, 14c of the 3-way valve 14 are fluidically connected with each other, while the first connector 14a is closed.

If now the fluid contained in the fluid conducting system is circulated, it flows, starting from the venous line section 2, through the 3-way valve 14, and from there, is again passed on in the arterial line section 4 without fluid being able to enter the fluid container 10. Consequently, the fluid stored in there remains uncontaminated.

After a predetermined time of recirculation, the 3-way valve 14 is put in the switch position shown in FIG. 5, in which again all three connectors 14a-14c are closed. You can see that the switch position according to FIG. 5 differs from the switch position according to FIG. 2 because the valve piston 20 was not simply turned back all the way in the first shut-off position according to FIG. 2, but was turned back in the second shut-off position according to FIG. 5, which is consequently diametrically opposite the first shut-off position. If the valve piston 20 had been turned back all the way, it would at least temporarily have passed through the "flush position", in which contaminated fluid from the fluid conducting system could possibly have penetrated the fluid container.

As soon as the 3-way valve 14 is closed, the venous line section 2 is now again disconnected from the 3-way valve 14 and the valve piston 20 is turned in the "single-pass" position according to FIG. 3 in order to flush the contaminated fluid from the fluid conducting system. Upon completion of this process, the filling/recirculation cycle is completed.

Then the 3-way valve 14 is closed again, all hose clamps 16, 18 are put in the shut-off position, and the arterial line section is also disconnected from the 3-way valve 14 so that it can be connected together with the venous line section to the patient's body.

In summary, the invention in hand concerns a recirculation device of an extracorporeal blood treatment device 1 with a preferably universal medical fluid container 10 to which an arterial line section 4 of a fluid conducting system of the extracorporeal blood treatment device 1 can be connected as an option. Furthermore, the recirculation device has a 3-way switch, preferably a 3-way valve 14, which is arranged directly downstream of the universal medical fluid container 10. A conduit 14a of the 3-way switch is coupled preferably with a spike 12 or a similar connecting device or is formed in one piece together with it.

The invention claimed is:

1. Recirculation device of an extracorporeal blood treatment device with a medical fluid container to which an arterial line section of a fluid conducting system of the extracorporeal blood treatment device can be connected, the recirculation device comprising:

a 3-way switch positioned downstream of the medical fluid container, the 3-way switch including a first conduit, a second conduit, and a third conduit, wherein,
the first conduit is configured to fluidly connect to a fluid chamber of the medical fluid container,
the second conduit is configured to fluidly connect to the arterial line section, and
the third conduit is configured to fluidly connect to a venous line section of the fluid conducting system,
the 3-way switch includes at least three positions, wherein,
in a first switch position, the first conduit is fluidly connected with the second conduit for fluid flow in between and the third conduit is closed
in a second switch position, the second conduit is fluidly connected with the third conduit for fluid flow in between and the first conduit is closed, and
in a third switch position, the first, second, and third conduits are closed, and
the 3-way switch is configured to perform a filling process and a recirculation process, wherein,
for the filling process, the medical fluid container is coupled with the arterial line section by placing the 3-way switch in the first switch position, and
for the recirculating process, the arterial line section is connected with the venous line section by placing the 3-way switch in the second switch position, wherein the first conduit is closed such that the medical fluid container is fluidly uncoupled from the fluid conducting system of the extracorporeal blood treatment device.

2. Recirculation device according to claim 1, wherein the first conduit is configured for fluid connection through a connection device or by having an integrated connection device.

3. Recirculation device according to claim 1, wherein the 3-way switch is a 3-way valve including a rotary piston with a handle for manually activating the 3-way valve.

4. Recirculation device according to claim 1, wherein, in the third switch position, the first, second, and third conduits are closed such that the arterial and venous line sections of the fluid conducting system are disconnected from the medical fluid container.

5. Recirculation device according to claim 1, further comprising a spike connected to or integrally formed with the first conduit of the 3-way switch, the spike adapted for connection with the medical fluid container.

6. Recirculation device according to claim 5, wherein the spike is directly connected to the first conduit transition-free without interposition of a bridging line section.

7. Recirculation device according to claim 1, wherein the medical fluid container is a universal container with exclusively one fluid outlet or one single tapping point.

8. Extracorporeal blood treatment device with an internal fluid conducting system that has an arterial line section and a venous line section for connecting the fluid conducting system to a patient, comprising a recirculation device according claim 1.

9. Use of a recirculation device according to claim 1 in a dialysis machine which has a patient-side fluid conducting system with the arterial line section and the venous line section that can be fluidly connected with the recirculation device to fill it.

10. Method for performing a filling and recirculation process of a blood-side conduit system of a dialysis machine using a recirculation device according to claim 1, the method comprising the steps of:

a. connecting the first conduit to the medical fluid container with the first, second, and third conduits closed, and connecting the arterial line section to the second conduit with the venous fluid section open to the environment;

b. flushing a fluid flow path along the arterial fluid conduit section of the extracorporeal blood treatment device and the venous fluid conduit section by fluidly connecting the medical fluid container with the second conduit of the 3-way switch;

c. completely closing the 3-way switch and connecting of the venous fluid conduit section with the third conduit of the 3-way switch, d. recirculating fluid in the fluid flow path by directly connecting the second and third conduits on the 3-way switch and simultaneously closing off the fluid source, e. complete closing the 3-way switch and uncoupling the venous fluid conduit section from the third conduit and repeatedly flushing the fluid flow path according to step b., and f. complete closing the 3-way switch in preparation for a subsequent connecting of the arterial and venous fluid conduit sections to a patient.

\* \* \* \* \*